United States Patent [19]

Ochsner

[11] 4,198,532
[45] Apr. 15, 1980

[54] NOVEL ALCOHOL ODORANTS

[75] Inventor: Paul A. Ochsner, Geneva, Switzerland

[73] Assignee: Givaudan Corporation, Clifton, N.J.

[21] Appl. No.: 927,809

[22] Filed: Jul. 25, 1978

[30] Foreign Application Priority Data

Aug. 4, 1977 [LU] Luxembourg ............................ 77923
Jun. 15, 1978 [CH] Switzerland ........................ 6537/78

[51] Int. Cl.² ...................... C07C 31/02; C07C 33/02
[52] U.S. Cl. ..................................... 568/840; 568/878;
568/884; 260/593 R; 252/522 R; 252/108;
424/69; 424/70; 252/174.11
[58] Field of Search ........................ 568/878, 884, 840

[56] References Cited

U.S. PATENT DOCUMENTS

| | | | |
|---|---|---|---|
| 2,838,576 | 6/1958 | Normant | 568/878 |
| 3,125,605 | 3/1964 | Buchner et al. | 568/884 |
| 3,308,172 | 3/1967 | Rudner et al. | 568/878 |
| 3,910,897 | 10/1975 | Chodneker et al. | 568/840 |
| 4,006,109 | 2/1977 | Ochsner et al. | 568/840 |
| 4,104,202 | 8/1978 | Wille | 568/840 |

OTHER PUBLICATIONS

Fieser et al., "Reagents for Organic Synthesis", pp. 582 & 1049 (1967).

*Primary Examiner*—Bernard Helfin
*Assistant Examiner*—James H. Reamer
*Attorney, Agent, or Firm*—Thomas Cifelli, Jr.; Robert F. Tavares

[57] ABSTRACT

Alcohols having the formula:

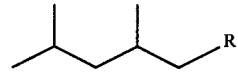

wherein R is 1-hydroxy-2-methyl-propyl or 3-hydroxybutyl, perfume compositions containing same and processes and intermediates involving same are disclosed.

4 Claims, No Drawings

NOVEL ALCOHOL ODORANTS

FIELD OF THE INVENTION

This invention relates to fragrances.

SUMMARY OF THE INVENTION

The present invention relates to novel odorants. More particularly, the invention is concerned with novel alcohols, a process for the manufacture thereof and odorant compositions containing same. The invention is also concerned with a method of imparting an odor to materials using said alcohols or compositions and to certain intermediates used in preparing said alcohols.

The novel alcohols provided by the present invention have the following general formula

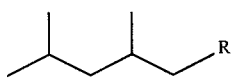

(I)

wherein R represents the 1-hydroxy-2-methylpropyl or 3-hydroxy-butyl group. Accordingly, formula I embraces 2,5,7-trimethyl-octan-3-ol (Ia) and 2,4-dimethyl-nonan-8-ol (Ib).

According to the process provided by the present invention, the alcohols of formula I hereinbefore are manufactured by (a) reacting 3,5-dimethylhexanal with an isopropyl-magnesium halide or reacting isobutyraldehyde with a 2,4-dimethylpentylmagnesium halide, or (b) hydrogenating 2,5,7-trimethyl-4-octen-3-ol or 6,8-dimethyl-3-nonen-2-ol, or 2,5,7-trimethyl-1,4-octadien-3-one- or 6,8-dimethyl-3,5-nonadien-2-one, or 2,5,7-trimethyl-3-octanone or 6,8-dimethyl-2-nonanone.

DESCRIPTION OF THE PREFERRED EMBODIMENTS

Embodiment (a) of the foregoing process, which leads exclusively to the alcohol Ia, can be carried out according to methods which are known per se for Grignard reactions. Thus, the reaction is conveniently carried out in diethyl ether as the solvent and at a temperature of 0°–10° C.

As the halides used in embodiment (a) of the process there come into consideration chlorides, bromides and iodides. Bromides and chlorides are especially suitable.

A hydrogenation in accordance with embodiment (b) of the process is conveniently carried out catalytically.

Where the octenol is catalytically hydrogenated, a Raney-nickel or palladium catalyst is conveniently used.

Palladium-on-carbon is the preferred catalyst.

The hydrogenation is conveniently carried out at room temperature, although it can also be carried out at a higher or lower temperature, and in a solvent such as ethyl acetate, ethanol, acetone etc.

Where the octanone or the 1,4-octadienone is catalytically hydrogenated, copper chromite or nickel is preferably used as the catalyst.

The octanone can also be reduced to the alcohol by means of sodium borohydride or lithium aluminium hydride (see L. F. Fieser & M. Fieser, Reagents for Organic Synthesis, John Wiley & Sons 1967, 582, 1049).

The catalytic hydrogenation of the 1,4-octadienone is conveniently carried out first at room temperature in order to hydrogenate the double bonds and then at an elevated temperature in order to hydrogenate the keto group. This latter hydrogenation can be carried out, for example, at a temperature of 120°–150° C., especially at ca 140° C.

In the case of the nonenol, there is preferably used starting material which is prepared in situ; for example, by catalytically hydrogenating 6,8-dimethyl-3-nonen-2-one using copper chromite.

Also, the 3,5-nonadienone is preferably hydrogenated using copper chromite.

The nonanone is conveniently reduced to the alcohol Ib using sodium borohydride or lithium aluminium hydride.

The 2,4-dimethylpentyl halides required for embodiment (a) of the process can be obtained by adding hydrogen halide to 2,4-dimethyl-1-pentene according to methods known per se in the presence of a peroxide or by replacing the primary alcoholic group of 2,4-dimethylpentanol, likewise in a manner known per se, by means of a phosphorus halogenide.

The novel keto compounds used in embodiment (b) of the process also form part of the present invention.

2,5,7-Trimethyl-1,4-octadien-3-one can be prepared, for example, from 2,4,7-trimethyl-7-octen-5-yn-4-ol by propargylic rearrangement in a manner known per se with the aid of a vanadium catalyst. By catalytically hydrogenating the resulting dienone at room temperature, as described hereinbefore, there is obtained 2,5,7-trimethyl-3-octanone. 6,8-Dimethyl-3-nonen-2-one can be prepared, for example, by aldol condensation of 3,5-dimethyl-hexanal with acetone.

The alcohols of formula I have particular organoleptic properties, on the basis of which they are excellently suited as odorant substances.

The invention is therefore also concerned with a method of imparting an odour to materials, which method comprises applying to said materials or incorporating therein an alcohol of formula I, especially in the form of mixtures. Moreover, the invention is also concerned with odorant compositions which contain an alcohol of formula I.

The alcohol Ia is characterised by interesting fruity (apricot-like) olfactory nuances. On the other hand, the alcohol Ib is characterised by a pleasant flowery, fruity, earthy-green, mushroom-like note, whereby aldehydic side-notes can be identified. The alcohols of formula I can therefore be used, for example, for the perfuming of products such as cosmetics (soaps, mouth washes, deodorants, shampoos, lotions, salves, powders etc), detergents etc, the alcohols preferably not being used alone but rather in the form of compositions which contain other odorant substances.

Of great advantage is the fact that 2,5,7-trimethyl-octan-3-ol brings about in bouquets of the widest variety of directions a velvet-like, rounding-off effect, which in this case can be substantially more important than the characteristic apricot-like odour. By adding 2,4-dimethyl-nonan-8-ol, which has an earthly, natural note, to compositions, there is produced a considerable intensification, and a radiance which comes into play especially in rose and jasmine notes. Since, moreover, the alcohols of formula I are saturated alcohols, they are extremely stable in mixtures.

On the basis of their high capability of blending harmoniously, the alcohols of formula I are suitable as odorants, especially in combination with a series of natural odorant substances such as, for example, galbanum oil, vetiver oil, patchouli oil, cedarwood oil, bergamotte oil, pine-needle oil, petitgrain oil, tree moss, lemon oil, coriander oil, angelica seed oil and cardamon oil.

The alcohol Ia can also be used advantageously in mixtures with mastix oil, palmarosa oil, jasmine absolute, mandarin oil and hyssop oil, while the alchol Ib on the other hand has desirable effects with ylang-ylang oil.

Owing to their radiance and naturalness, the two alcohols provided by the present invention can advantageously be used for the production of compositions with, for example, the following synthetic odorant substances:

aldehydes such as hydroxycitronellal, n-decanal, 2,4-dimethyl-3-cyclohexenyl-1-carboxaldehyde, substituted cinnamaldehydes, 3,5,6-trimethyl-3-cyclohexene-1-carboxaldehyde, p-tert.butyl-α-methylhydrocinnamaldehyde, p-isopropyl-α-methylhydrocinnamaldehyde, p-tolyl-acetaldehyde, α-methyl-3,4-methylenedioxy-hydrocinnamaldehyde, 2,6-dimethyl-5-heptenal etc;

ketones such as 7-acetyl-1,1,3,4,4,6-hexamethyltetrahydro-(1,2,3,4)-naphthalene, α-ionone, allyl-α-ionone, musk ketone, p-methylacetophenone etc;

acetals such as 1-phenyl-4-methyl-3,5-dioxaoctane, phenylacetaldehyde dimethylacetal etc;

phenolic compounds such as eugenol etc;

alcohols such as phenylethyl alcohol, linalool, citronellol, cis-6-nonenol, cinnamic alcohol, phenylpropyl alcohol, geraniol, nerol etc;

ethers such as 1-methylcyclododecan-1-yl methyl ether, 8α,12-oxido-13,14,15,16-tetranorlabdane etc;

esters such as benzyl acetate, ethyl α-methylphenylglycidate, linalyl acetate, vetivenyl acetate, linalyl anthranilate, methyl dihydrojasmonate, benzyl salicylate, 2-tert.butylcyclohexyl acetate, ethyl acetoacetate, dimethylbenzylmethyl butyrate, 5-[4- or 5-(acetoxymethyl)-1-cyclohexenyl]-2-methyl-2-pentene, hexenyl salicylate, hexenyl acetate, benzyl propionate, phenoxyethyl isobutyrate, p-cresyl phenylacetate, cinnamyl formate, geranyl acetate, styrallyl acetate, phenylethyl formate etc;

lactones such as coumarin, γ-undecalactone, γ-nonalactone etc;

sulphur-containing compounds such as p-menthane-8-thiol-3-one, sulphides etc; and nitrogen-containing compounds such as indole, 5-methyl-3-heptanonoxime, dimethylpyrazine etc.

The alcohols Ia and Ib can accordingly be used for the production of compositions and, as will be evident from the foregoing, they can be used together with a wide range of known odorant substances. The alcohols Ia and Ib are especially useful for the production of compositions having fruity, flowery, green, woody, chypre-like and cologne-like notes.

The odorant compositions produced with the alcohols of formula I are especially attractive by the remarkable radiance, naturalness and liveliness.

Thus, for example, the alcohol Ia is able to enrich flowery-fruity perfume compositions with additional radiance and naturalness and thus comes to meet the tendencies of modern perfumery in a welcomed manner. The alcohol Ia elevates the hesperidine note in fresh, citrus-like, woody compositions in an advantageous manner and at the same time underlines the woody character in an improved way. It can generally be stated that Ia, for example, shows very good effects in distinctly feminine perfumes, but on the other hand is also used with advantage in masculine compositions. Interesting flower complexes can also be produced with the aid of the alcohol Ia and this alcohol can combine well with pinewood notes.

The alcohol Ib possesses a natural, mushroom-like characteristic odour reminiscent of humid forests. On the basis of this property there is obtained by means of the alcohol Ib, for example in jasmine or rose compositions, a distinct intensification of the desired natural character of the perfume. The radiance which the alcohol Ib confers to compositions is especially valuable in the production of compositions which are used in industrial perfumery such as, for example, in the perfuming of soaps and washing powders.

The concentration of the alcohols of formula I can vary within wide limits depending on the purpose of use; for example, between about 0.01 wt.% in the case of detergents and about 15 wt.% in the case of alcoholic solutions. In perfume bases or concentrates the concentrations can, of course, also be higher. The perfume bases can be used in the customary manner for the perfuming of Eau de Cologne, eau de toilette, lotions, creams, shampoos, soaps, detergents etc.

With low concentrations (e.g. 0.5–2%), of an alcohol of formula I there can already be established a distinct increase in the radiance without the basic character of the composition being substantially altered. With high concentrations (e.g. 10%–30%) there also sets in a modification corresponding to the olfactory properties of the particular alcohol used.

The following Examples illustrate the process provided by the present invention:

EXAMPLE 1

26.4 g (1.1 gram atom) of magnesium shavings and 100 ml of dry ether are added to a round flask which is provided with a stirrer, condenser, thermometer and dropping funnel. There is now slowly added thereto a solution of 86.4 g (1.1 mol) of isopropyl chloride in 150 ml of anhydrous ether and the mixture is held at reflux temperature. The reaction is initiated by the addition of a small amount of iodine to the magnesium. After completion of the addition of the isopropyl chloride, the mixture is held for a further 1 hour at reflux temperature. There are now slowly added thereto at 5° C. 128.2 g (1 mol) of 3,5-dimethylhexanal dissolved in 250 ml of anhydrous ether. The mixture is again held for 3 hours at reflux temperature. The mixture is then cooled down to 0° C. and the product is decomposed by the addition of 340 ml of ice-cold 10% hydrochloric acid. The ethereal solution is washed neutral with water and dried, and the solvent is evaporated. There are thus obtained 176 g (70%) of crude product, fractional distillation of which yields 121.4 g of 2,5,7-trimethyl-octan-3-ol of boiling point 79° C./5 mmHg; $n_D^{20}=1.4362$.

EXAMPLE 2

(a) 26.4 g (1.1 gram atom) of magnesium shavings and 100 ml of anhydrous ether are added to a round flask which is provided with a stirrer, condenser, thermometer and dropping funnel. There is now slowly added thereto a solution of 90.2 g (1.15 mol) of isopropyl chloride in 150 ml of ether. After completion of the addition, the mixture is held at reflux temperature for a further 1 hour. There are now added thereto at a temperature of 10° C. 126.2 g (1 mol) of 3,5-dimethyl-2-hexenal dissolved in 250 ml of anhydrous ether. The mixture is held at reflux temperature for 3 hours, then cooled down to 0° C. and decomposed by the addition of 370 ml of 10% ice-cold hydrochloric acid. The ethereal solution is washed neutral with water and dried, and the solvent is evaporated. There are thus obtained 168 g of crude material, fractional distillation of which yields 123.7 g (72.6%) of 2,5,7-trimethyl-4-octen-3-ol of boiling point 78°–79° C./5 mmHg; $n_D^{20} = 1.4526$.

(b) 100 g of the foregoing octenol dissolved in 200 ml of ethyl acetate are hydrogenated in the presence of 10 g of 5% palladium-on-carbon. After uptake of 5.08 liters of hydrogen at 20° C. (theoretical amount = 14.6 liters) and at atmospheric pressure, the hydrogen uptake ceases. The catalyst is removed by filtration, the solvent is evaporated and the hydrogenation is completed in an autoclave in the presence of 1 g of Raney nickel at 100° C./10 atmospheres. After 2 hours, the mixture is allowed to cool down, the catalyst is filtered off and the product is distilled. There are thus obtained 63 g of 2,5,7-trimethyl-octan-3-ol of boiling point 72° C./5 mmHg; $n_D^{20} = 1.4362$; $d_4^{20} = 0.8287$. The yield amounts to 62.5%.

EXAMPLE 3

(a) 400 ml of anhydrous toluene and 200 g of powdered potassium hydroxide are added to a 2 liter round flask which is provided with a stirrer, condenser, thermometer and dropping funnel. The mixture is cooled to −20° C. and there are now added thereto at a temperature between −20° C. and −10° C. 66g (1 mol) of 3-methyl-3-buten-1-yne [A. F. Thompson jun. N. A. Milas, Ida Rovno, J. Am. Chem. Soc. 63, (1941), 752–755]. The mixture is held at a temperature of −10° C. for 1.5 hours while stirring and there are slowly added thereto at 0° C. 110 g (1.1 mol) of methyl isobutyl ketone. The mixture is now stirred at 0° C. for 1 hour and then the temperature is allowed to rise to 20° C. within 2 hours with further stirring. The mixture is added to ice, extracted with 500 ml of toluene and washed with brine until neutral. The solvent is then evaporated. There are obtained 183 g of crude product, distillation of which yields 129.5 g (78.4%) of 2,4,7-trimethyl-7-octen-5-yn-4-ol of boiling point 76°–77° C./5 mmHg; $n_D^{20} = 1.4690$; $d_4^{20} = 0.8620$.

(b) 880 g of paraffin oil are added to a 2 liter round flask which is provided with a thermometer, stirrer and condenser. This is heated to 140° C. for 1 hour at a pressure of 0.1 mmHg for the purpose of degasification.

After cooling down to 30° C., there are added thereto 75 g of triphenylsilanol, 2 g of stearic acid, 7.6 ml of triisopropyl vanadate and 100 g of the foregoing octenynol. The mixture is now heated to 140° C. for 2 hours under a nitrogen atmosphere and again allowed to cool down to 80° C. The resulting crude ketone is distilled off at a temperature of 50°–70° C. The distillation is continued until an internal temperature of 150° C. and a vacuum of 1 mmHg is attained. There are thus obtained 71 g (71%) of crude 2,5,7-trimethyl-1,4-octadien-3-one (z+e); $n_D^{20} = 1.4736$. The constants of the distilled pure product are as follows: Boiling point = 77° C./5 mmHg; $n_D^{20} = 1.4742$; $d_4^{20} = 0.8674$.

(c) 16.6 g of the crude ketone are hydrogenated in 250 ml of methanol at atmospheric pressure and 20° C. in the presence of 3 g of Raney nickel and 1 g of sodium carbonate. After uptake of 4.84 liters of hydrogen (theoretical amount = 7.5 liter)s, the hydrogen uptake ceases. The catalyst is filtered off, the methanol is evaporated off and the product, containing 2,5,7-trimethyl-3-octanone, is added to an autoclave together with 3 g of Raney nickel and 1 g of sodium carbonate. After 48 hours at 140° C. and a hydrogen pressure of 40 atmospheres, the hydrogenation is complete. There are obtained 14 g (67%) of crude product, distillation of which yields 11.5 g of 2,5,7-trimethyl-octan-3-ol of boiling point 72° C./5 mmHg; $n_D^{20} = 1.4362$; $d_4^{20} = 0.8287$.

EXAMPLE 4

(a) 112 g of 2,4-dimethyl-2-pentenal and 5 g of copper chromite are added to a stainless steel autoclave of 300 ml capacity. The mixture is held at a pressure of 25 atmospheres of hydrogen and a temperature of 150° C. After 8 hours, the theoretical amount of hydrogen is taken up, namely 50 liters (calculated at atmospheric pressure). The catalyst is removed by filtration and the resulting 108 g of crude product are distilled. There are obtained 90.7 g (78.3%) of 2,4-dimethylpentanol of boiling point 81° C./34 mmHg; $n_D^{20} = 1.4232$; $d_4^{20} = 0.8199$.

(b) 116 g (1 mol) of the foregoing pentanol and 12 g of anhydrous pyridine are added to a round flask which is provided with a stirrer, thermometer, condenser and dropping funnel. There are now slowly added thereto while cooling 110 g (0.4 mol) of phosphorus tribromide. During the addition the temperature is held below 60° C., but after the addition the mixture is held at 60° C. for a further 1 hour. After cooling down, the mixture is taken up in ether, the ethereal solution is washed with water, then with a 8% sodium bicarbonate solution and again with water until neutral. The solution is dried over anhydrous sodium sulphate and the solvent is evaporated off. There are obtained 206 g of crude bromide, distillation of which yields 111.5 g (62.3%) of 2,4-dimethylpentyl bromide (1) of boiling point 70° C./40 mmHg; $n_D^{20} = 1.4495$; $d_4^{20} = 1.1376$.

(c) 9 g of magnesium shavings and 50 ml of anhydrous ether are added to a round flask which is provided with a stirrer, thermometer, condenser and dropping funnel. There is now slowly added thereto at the boiling point of the ether a solution of 72.2 g of the foregoing bromide in 100 ml of anhydrous ether. The mixture is heated to reflux temperature for 0.5 hour and then cooled down to 0° C. There is now added thereto at a temperature of 10° C. a solution of 27.6 g of isobutyraldehyde in 60 ml of dry ether. The mixture is brought to reflux temperature for 3 hours and again cooled down. The mixture is decomposed by the addition of 20% ammonium chloride solution. The mixture is extracted with ether, washed successively with a 10% tartaric acid solution, water, 10% sodium carbonate solution and water until neutral. The solution is dried over anhydrous sodium sulphate and the solvent is evaporated off. There are obtained 56.6 g of crude material, distillation of which yields 32 g (46.2%) of 2,5,7-trimethyl-octan-3-ol of boiling point 78° C./6 mmHg; $n_D^{20} = 1.4370$; $d_4^{20} = 0.8287$.

EXAMPLE 5

(a) 128 g of 3,5-dimethyl-hexanal and 58 g of acetone are placed in a round flask which is provided with a stirrer, condenser, thermometer and dropping funnel. The mixture is heated to 80° C. At this temperature there are added dropwise over a period of 1 hour while stirring 150 ml of 1-N sodium hydroxide solution. After the addition, the mixture is held at 80° C. for a further 0.25 hour. After cooling down, the mixture is taken up in 200 ml of ether and washed with water until neutral. After evaporation of the solvent, there are obtained 147 g of crude product which is fractionated by distillation. The first fractions (34 g) consist of the aldehyde starting material (boiling point 33° C./8 mmHg). The second part of the distillate (28 g) is the desired condensation product 6,8-dimethyl-3-nonen-2-one (boiling point 88° C./6 mmHg). The third part (55 g) consists of the addition product 6,8-dimethyl-4-hydroxy-nonan-2-one (boiling point 106°-108° C./6 mmHg) which is dehydrated as follows:

55 g of 6,8-dimethyl-4-hydroxy-nonan-2-one are distilled at 92°-103° C. in a Claisen flask over 2 g of potassium hydrogen sulphate under a vacuum of 18 mmHg. The distillate is taken up in 100 ml of ether and washed with sodium hydrogen carbonate solution and then with water. After distillation of the solvent, there are obtained 43 g of crude product which, upon distillation, give 40 g of 6,8-dimethyl-3-nonen-2-one of boiling point 88° C./6 mmHg. The total yield of 6,8-dimethyl-3-nonen-2-one amounts to 71 g (42%).

64 g of the foregoing ketone are hydrogenated in a stirring autoclave in the presence of 6 g of copper chromite and under 40 bar hydrogen pressure. The temperature is firstly brought to 140° C. When the hydrogen absorption slows down (after 3 hours), the autoclave is heated to 170° C. and held for 3 hours between 165° C. and 170° C. After cooling down to 25° C., the catalyst is filtered off under suction and the filtrate is distilled. There are obtained 56 g (85.4%) of chemically pure 2,4-dimethyl-nonan-8-ol.

(b) 58, 9 g of 6,8-dimethyl-3-nonen-2-one, 25 ml of water and 70 ml of ethanol are added to a 250 ml round flask which is provided with a stirrer and a thermometer. 8 g of sodium borohydride are added slowly while maintaining the temperature below 25° C. by cooling with a cold water bath. The mixture is now stirred at 25° C. for 3 hours. 50 ml of a saturated solution of tartaric acid and 100 ml of ether are added to the reaction mixture. The organic layer is then washed with brine until neutral. The solvent is evaporated. There are obtained 58 g of crude product, distillation of which yields 45 g (76,2%) of 6,8-dimethyl-3-nonen-2-ol of boiling point 88°-90° C./5 mm; $n_D^{20}=1,4435$; $d_4^{20}=0,8330$.

6,8-Dimethyl-3-nonen-2-ol has a fruity, flowery, green and mushroom like odor. It can be used as a fragrance ingredient the same way as a compound of formula I.

34 g of the foregoing nonenol dissolved in 80 ml of ethyl acetate are hydrogenated in the presence of 4 g of 5% palladium-on-carbon. After uptake of the theoretical amount of 5 liters of hydrogen at 20° C. and at atmospheric pressure, the hydrogen uptake ceases. The catalyst is removed by filtration, the solvent is evaporated. There are obtained 37 g of crude product, distillation of which yields 31 g of chemically pure 2,4-dimethyl-nonan-8-ol.

EXAMPLE 6

200 g of freshly distilled 6,8-dimethyl-3,5-nonadien-2-one and 2 g of copper chromite are placed in a 1 liter steel autoclave which is provided with a magnetic stirrer (Autoclave Engineers, Inc.). The autoclave is flushed with hydrogen and it is firstly placed under a pressure of 30 bar of hydrogen. The autoclave is now heated rapidly to 100° C. and then slowly within 3 hours to 170° C. The pressure is then adjusted to 50 bar and the temperature is fixed at 200° C. The theoretical amount of hydrogen to be absorbed amounts to 90 liters. The autoclave is held at a pressure of 50 atmospheres and in a temperature range between 180°-200° C. After 5 hours, 7% of unsaturated material is still present in the mixture. The hydrogenation is continued for a further 6 hours in order to reduce the amount of non-hydrogenated product to 0.2%. The resulting crude product is separated from the catalyst by filtration and then distilled. There are obtained 171 g (83%) of chemically pure 2,4-dimethyl-nonan- 8-ol of boiling point 91° C./6 mmHg; $n_D^{20}=1.4368$. 136 g of this product are designated at being olfactorily good (yield 83% or 65.7% respectively).

The following Example illustrates typical odorant compositions provided by the present invention:

Example A (A) Base having a fruit character

|  | Parts by weight |
|---|---|
| Benzyl acetate | 100 |
| α-Amylcinnamaldehyde | 100 |
| Phenylethyl alcohol | 100 |
| Fraise (Trade Mark) (ethyl α-methylphenylglycidate) | 60 |
| Lilial (Trade Mark) (p-tert.butyl-α-methylhydro-cinnamaldehyde) | 40 |
| Fixolid (Trade Mark) [7-acetyl-1,1,3,4,4,6-hexamethyl-tetra-hydro(1,2,3,4)-naphthalene] | 80 |
|  | 480 |

The mixture is initially "synthetic" and not rounded-off. When there are added thereto 100 parts by weight of 2,5,7-trimethyl-octan-3-ol there is obtained a very pleasant, rich, remarkably natural perfume composition in which the fruity character dominates.

(B) Muguet base

|  | Parts by weight |
|---|---|
| Cyclamenaldehyde (Trade Mark) (p-isopropyl-α-methylhydro-cinnamaldehyde) | 10 |
| p-Tolylacetaldehyde | 5 |
| α-Amylcinnamaldehyde | 100 |
| Phenylethyl alcohol | 70 |
| Linalool | 50 |
| Linalyl acetate | 50 |
| Fixolid (Trade Mark) | 80 |
| Laurin (Trade Mark) (hydroxy-dihydrocitronellal) | 300 |
|  | 665 |

This composition has a good lily of the valley character and tends in the direction of lilac, but it is, however, initially "synthetic" and somewhat aggressive. After the addition of 100 parts by weight of 2,5,7-trimethyl-octan-3-ol, a velvet-like impression predominates and the note is now rounded-off and fruity.

(C) Fougère base

|  | Parts by weight |
|---|---|
| Lavender oil (French) | 60 |
| Linalyl acetate | 50 |
| Coumarin | 50 |
| Phenylethyl alcohol | 80 |
| Hydroxycitronellal | 80 |

| -continued | Parts by weight |
|---|---|
| oak moss (Yugoslavian) | 30 |
| Vetivenyl acetate (Trade Mark) | 30 |
| Sandalwood oil | 40 |
| α-Amylcinnamaldehyde | 80 |
| Linalool | 60 |
| | 560 |

When there are added to this base 120 parts by weight of 2,5,7-trimethyl-octan-3-ol, the green, aggressive note is suppressed and there is obtained a uniform, rounded-off, fruity odour.

(D) Perfumery base having a green note

| | Parts by weight |
|---|---|
| Stemon (5-methyl-3-heptanonoxime) | 5 |
| Galbanum oil | 5 |
| Corps Cassis (Trade Mark) (8-mercapto-p-menthan-3-one) 1°/$_{oo}$ in ethyl citrate) | 5 |
| Mastix oil absolute | 10 |
| Cyclal C (Trade Mark) (2,4-dimethyl-3-cyclohexenyl-1-carboxaldehyde) (10% in propyleneglycol) | 15 |
| Basil oil | 30 |
| Linalyl anthranilate | 20 |
| Methyl dihydrojasmonate | 50 |
| Benzyl salicylate | 90 |
| α-Hexyl cinnamaldehyde | 90 |
| Linalyl acetate | 90 |
| CD-acetal (Trade Mark) (phenylacetaldehyde glycerinacetal) | 40 |
| 2,5,7-Trimethyl-octan-3-ol | 50 |
| | 500 |

The presence of 2,5,7-trimethyl-octan-3-ol confers to the composition a pleasant, rounded-off character which is clearly missing without this alcohol.

(E) Chypre base

| | Parts by weight |
|---|---|
| Coriander oil | 20 |
| Madrox (Trade Mark) (1-methyl-cyclododecan-1-yl methyl ether) | 65 |
| Patchouli oil | 30 |
| Hydroxycitronellal | 30 |
| Bergamotte oil | 50 |
| Pine-needle oil | 20 |
| Galbanum oil | 20 |
| Angelica seed oil | 10 |
| Cardamom oil | 5 |
| α-Ionone | 25 |
| Lemon oil (Italian) | 15 |
| Tree moss (50% in propyleneglycol) | 30 |
| Petitgrain oil | 20 |
| Heliional (Trade Mark) (α-methyl-3,4-methylenedioxy-hydro-cinnamaldehyde) | 20 |
| Vetiver oil Bourbon | 5 |
| Citronellol | 10 |
| Cedarwood oil | 20 |
| Coumarin | 5 |
| 2,5,7-Trimethyl-octan-3-ol | 100 |
| | 500 |

The addition of 2,5,7-trimethyl-octan-3-ol intensifies the fruity note of the composition. It is fuller, more powerful and gives a rounded-off, pleasant impression.

(F) Perfumery base having an apricot note

| | Parts by weight |
|---|---|
| α-Ionone | 80 |
| Dimethylbenzylmethyl butyrate | 50 |
| Allyl-α-ionone | 40 |
| Ethyl acetoacetate | 30 |
| Palmarosa oil | 20 |
| γ-Undecalactone | 15 |
| Galaxolid (Trade Mark) (1,3,4,6,7,8-hexahydro-4,6,6,7,8,8-hexamethyl-cyclopenta-γ-2-benzopyran) | 10 |
| Propyleneglycol | 230 |
| 2,5,7-Trimethyl-octan-3-ol | 25 |
| | 500 |

Although this composition has a fruity character without 2,5,7-trimethyl-octan-3-ol, the addition of 2,5,7-trimethyl-octan-3-ol intensifies and improves the fruity note in the direction of apricots, the natural effect of ripe apricots is produced.

(G) Perfumery base having a melon note

| | Parts by weight |
|---|---|
| Myraldyl acetate [5-[4- or 5-(acetoxymethyl)-1-cyclohexenyl]-2-methyl-2-pentene] | 80 |
| Hexenyl salicylate | 70 |
| Cyclamenaldehyde (Trade Mark) | 60 |
| Ethyl acetoacetate | 50 |
| Cis-6-nonenol (10% in propyleneglycol) | 30 |
| Hexenyl acetate (10% in propyleneglycol) | 20 |
| Melonal (Trade Mark) (2,6-dimethyl-5-heptenal) (10% in propyleneglycol) | 50 |
| Lilial (Trade Mark) | 20 |
| Propyleneglycol | 20 |
| 2,5,7-Trimethyl-octan-3-ol | 100 |
| | 500 |

The presence of 100 parts by weight of 2,5,7-trimethyl-octan-3-ol gives to the mixture a natural, rounded-off character, the typical note of ripe melons is better recognisable.

(H) Base resembling citrus fruit

| | Parts by weight |
|---|---|
| Bergamotte oil | 300 |
| Corps Cassis (Trade Mark) (8-mercapto-p-menthan-3-one) (1°/$_{oo}$ in ethyl citrate) | 300 |
| Mandarin oil | 150 |
| Galbanum oil | 120 |
| Dimethylpyrazine (10% in propyleneglycol) | 10 |
| 2,5,7-Trimethyl-octan-3-ol | 120 |
| | 1000 |

Without the addition of 2,5,7-trimethyl-octan-3-ol the mixture is "sharp" and aggressive. With the alcohol there is obtained a rounded-off, more pleasant composition which is especially suitable for perfumery purposes.

(I) Base resembling sage oil

|  | Parts by weight |
| --- | --- |
| Bergamotte oil | 120 |
| Hyssop oil | 80 |
| Patchouli anhydrol | 80 |
| Allyl-α-ionone | 30 |
| 8α,12-Oxido-13,14,15,16-tetra-norlabdane | 5 |
| 2,5,7-Trimethyl-octan-3-ol | 185 |
|  | 500 |

With 185 parts by weight of 2,5,7-trimethyl-octan-3-ol there is obtained a mixture having an original effect which distinctly accentuates the sage character. The note is sought after in modern perfumery.

(K) Jasmine base

|  | Parts by weight |
| --- | --- |
| Benzyl acetate | 400 |
| α-Hexylcinnamaldehyde | 200 |
| Benzyl propionate | 50 |
| Ylang-ylang oil | 50 |
| Linalool | 50 |
| Phenoxyethyl isobutyrate | 50 |
| Phenylethyl alcohol | 30 |
| p-Cresyl phenyl acetate (10% in propyleneglycol) | 30 |
| Undecalactone (10% in propyleneglycol) | 20 |
| Indole (10% in propyleneglycol) | 20 |
|  | 900 |

When there are added to this classical jasmine base 100 parts by weight of 2,4-dimethyl-nonan-8-ol, there results a base which is now not only more natural, but also has a rounded-off flowery character.

This flowery base is especially suitable for the perfumery of soaps and washing powders. At a concentration of 1% to 1.5% parts by weight in soaps the composition behaves like an extremely stable powerful perfume. In washing powders the optimum effect is achieved at a concentration of 0.1% to 0.3%, the flowery note then being particularly emphasised by the presence of 2,4-dimethyl-nonan-8-ol.

(L) "Rose" composition

|  | Parts by weight |
| --- | --- |
| Phenylethyl alcohol | 300 |
| Geraniol | 200 |
| Citronellol | 200 |
| Fixolid (Trade Mark) [7-acetyl-1,1,3,4,4,6-hexamethyl-tetrahydro(1,2,3,4)-naphthalene] | 100 |
| Nerol | 50 |
| Phenylacetic acid | 5 |
|  | 855 |

This composition is a "common" rose composition. When 145 parts by weight of 2,4-dimethyl-nonan-8-ol are now added thereto, there is obtained a base having much more body which is natural and especially reminiscent of rose petals and of the "Rose of May" (cross between Rosa centifolia and Rosa gallica).

(M) Chypre base

|  | Parts by weight |
| --- | --- |
| Coriander oil | 40 |
| Madrox (Trade Mark) (1-methyl-cyclododecan-1-yl methyl ether) | 130 |
| Patchouli oil | 60 |
| Hydroxycitronellal | 60 |
| Bergamotte oil | 100 |
| Pine-needle oil | 40 |
| Galbanum oil | 40 |
| Angelica seed oil | 20 |
| Cardamon oil | 10 |
| α-Ionone | 50 |
| Lemon oil (Italian) | 30 |
| Tree moss (50% in propyleneglycol) | 60 |
| Petitgrain oil | 40 |
| Helional (Trade Mark) (α-methyl-3,4-methylenedioxy-hydro-cinnamaldehyde | 40 |
| Vetiver oil Bourbon | 10 |
| Citronellol | 20 |
| Cedarwood oil | 40 |
| Coumarin | 10 |
|  | 800 |

This classical chypre base is distinctly improved by the addition of 100 parts by weight of 2,4-dimethyl-nonan-8-ol in that there results a flowery and green nuance and the (desired) odour of undergrowth is intensified.

(N) Lilac base

|  | Parts by weight |
| --- | --- |
| Terpineol | 260 |
| Hydroxycitronellal | 200 |
| Phenylethyl alcohol | 160 |
| Cinnamic alcohol (substitute) | 100 |
| Phenylpropyl alcohol | 100 |
| Cinnamyl formate | 20 |
| Geranyl acetate | 10 |
| Musk ketone | 10 |
| Jasmine oil (substitute) | 10 |
| Eugenol | 5 |
| Indole (10% in propyleneglycol) | 5 |
| p-Methylacetophenone | 5 |
| γ-Undecalactone | 5 |
| Corps Cassis (Trade Mark) (8-mercapto-p-menthan-3-one) (1°/00 in ethyl citrate) | 5 |
| n-Decanal (10% in propyleneglycol) | 5 |
| 2,4-Dimethyl-nonan-8-ol | 100 |
|  | 1000 |

By the addition of 100 parts by weight of 2,4-dimethyl-nonan-8-ol the conventional lilac base takes on an earthy nuance which makes the formerly "synthetic" odour more balanced, flowery and natural.

(O) Cologne for men

|  | Parts by weight |
| --- | --- |
| Linalool | 50 |
| Angelica seed oil | 10 |
| Cardamom oil | 5 |
| Pine-needle oil | 50 |
| Hydroxycitronellal | 70 |
| α-Ionone | 30 |
| Bergamotte oil | 80 |
| Patchouli oil | 30 |
| Tree moss (50% in propyleneglycol) | 30 |
| Cyclal C (Trade) (2,4-dimethyl-3-cyclohexenyl-1- |  |

-continued

| | Parts by weight |
|---|---|
| carboxaldehyde) (10% in propyleneglycol) | 5 |
| Styrallyl acetate | 5 |
| Petitgrain oil | 20 |
| Citronellol | 25 |
| Madrox (Trade Mark) (1-methyl-cyclododecan-1-yl methyl ether) | 50 |
| 2,4-Dimethyl-nonan-8-ol | 40 |
| | 500 |

In this composition the 2,4-dimethyl-nonan-8-ol brings about a rounding-off effect. The composition containing 2,4-dimethyl-nonan-8-ol is less "harsh", but more powerful, it is much more suitable for perfumery purposes.

(P) Perfumery base having a green note

| | Parts by weight |
|---|---|
| α-Hexylcinnamaldehyde (substitute) | 200 |
| Phenylethyl formate | 200 |
| Galbanum oil (synthetic) | 60 |
| Acetal R (Trade Mark) (1-phenyl-4-methyl-3,5-dioxaoctane) | 60 |
| Isocyclocitral (Trade Mark) (3,5,6-trimethyl-3-cyclohexene-1-carboxaldehyde) | 60 |
| 2-Tert.butylcyclohexyl acetate | 40 |

-continued

| | Parts by weight |
|---|---|
| Cyclal C (Trade Mark) (2,4-dimethyl-3-cyclohexenyl-1-carboxaldehyde) (10% in propyleneglycol) | 20 |
| Stemon (Trade Mark) (5-methyl-3-heptanonoxime) | 10 |
| Lemon oil | 10 |
| Propyleneglycol | 140 |
| 2,4-Dimethyl-nonan-8-ol | 200 |
| | 1000 |

The absence of 2,4-dimethyl-nonan-8-ol from the composition gives a flowery, but "synthetic", "chemical" impression. The addition of 2,4-dimethyl-nonan-8-ol confers an earthy, natural character to the base.

What is claimed is:
1. Alcohols of the general formula:

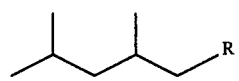

(I)

wherein R represents the 1-hydroxy-2-methyl-propyl or 3-hydroxy-butyl group.

2. An alcohol according to claim 1 having the formula: 2,5,7-trimethyl-octan-3-ol.

3. An alcohol according to claim 1 having the formula: 2,4-dimethyl-nonan-8-ol.

4. 6,8-Dimethyl-3-nonen-2-ol.

* * * * *